United States Patent [19]

Stein et al.

[11] Patent Number: 5,715,820
[45] Date of Patent: Feb. 10, 1998

[54] X-RAY BONE DENSITOMETRY USING MULTIPLE PASS SCANNING WITH IMAGE BLENDING

[75] Inventors: Jay A. Stein, Farmingham; Noah Berger, Waltham; Richard E. Cabral, Tewksbury, all of Mass.

[73] Assignee: Hologic, Inc., Waltham, Mass.

[21] Appl. No.: 465,736

[22] Filed: Jun. 6, 1995

[51] Int. Cl.⁶ .................................................. A61B 5/00
[52] U.S. Cl. ..................... 128/653.1; 378/146; 378/196; 378/62; 378/55; 250/370.09
[58] Field of Search .................................. 378/54, 55, 56, 378/112, 197, 207, 205, 209, 98.9; 128/653.1, 781; 250/370.08, 370.09

[56] References Cited

U.S. PATENT DOCUMENTS

| | | |
|---|---|---|
| 3,803,417 | 4/1974 | Kok . |
| 3,944,830 | 3/1976 | Dissing . |
| 3,988,585 | 10/1976 | O'Neill et al. . |
| 4,144,457 | 3/1979 | Albert . |
| 4,358,856 | 11/1982 | Stivender et al. . |
| 4,365,343 | 12/1982 | Grady et al. . |
| 4,649,560 | 3/1987 | Grady et al. . |
| 4,715,057 | 12/1987 | Hahn et al. . |
| 4,716,581 | 12/1987 | Barud . |
| 4,788,429 | 11/1988 | Wilson . |
| 4,811,373 | 3/1989 | Stein . |
| 4,829,549 | 5/1989 | Vogel et al. . |
| 4,903,203 | 2/1990 | Yamashita et al. . |
| 5,040,199 | 8/1991 | Stein . |
| 5,070,519 | 12/1991 | Stein et al. . |
| 5,132,995 | 7/1992 | Stein . |
| 5,148,455 | 9/1992 | Stein . |
| 5,155,756 | 10/1992 | Pare et al. . |
| 5,165,410 | 11/1992 | Warne et al. . |
| 5,172,695 | 12/1992 | Cann et al. . |
| 5,177,776 | 1/1993 | Ohmori et al. . |
| 5,228,068 | 7/1993 | Mazess . |
| 5,287,546 | 2/1994 | Tesic et al. . |
| 5,291,537 | 3/1994 | Mazess . |
| 5,305,368 | 4/1994 | Bisek et al. . |
| 5,306,306 | 4/1994 | Bisek et al. . |
| 5,432,834 | 7/1995 | Gershman . |

FOREIGN PATENT DOCUMENTS

| | | |
|---|---|---|
| 0026494 | 4/1981 | European Pat. Off. . |
| 0432730 | 6/1991 | European Pat. Off. . |
| 0461028 | 12/1991 | European Pat. Off. . |
| 0713676 | 5/1996 | European Pat. Off. . |
| 2238706 | 2/1974 | Germany . |
| WO8607531 | 12/1986 | WIPO . |
| WO9421174 | 9/1994 | WIPO . |

OTHER PUBLICATIONS

Lunar, A Quantum Leap in Bone Densitometry, Expert, The World's First Imaging Densitometer (undated by beleived to have been published before Nov. 22, 1992).

(List continued on next page.)

*Primary Examiner*—Marvin M. Lateef
*Assistant Examiner*—Eleni Mantis Mercader
*Attorney, Agent, or Firm*—Cooper & Dunham LLP

[57] ABSTRACT

The system of the present invention uses x-rays having a narrow fan beam to scan patients for bone density and soft tissue body composition measurement and imaging. In addition to single pass scanning of body parts such as the spine, hip and forearm, a method for multiple pass whole body scanning is provided. The system includes a movable scan table configured to support a patient and a C-arm associated with the table. The C-arm is configured to support an x-ray source in opposite to an x-ray detector at opposite sides of the patient. A scanning mechanism is provided to move the scan table and C-arm to scan the patient with overlapping adjacent x-ray fan beams in successive scan passes along the length of the patient. A scan pass combination scheme that blends areas of overlap is employed to compensate errors related to height dependency. The blending is performed according to the height of the part of patient scanned in the overlap and the distance from the edge of the scan pass.

10 Claims, 9 Drawing Sheets

OTHER PUBLICATIONS

Lunar News, Dec. 1992, "Lunar Introduces Expert, the World's First Imaging Densitometer".

Product Information, Expert, Today's Breakthrough – Tomorrow's Standard (undated, but believed to have been published before Nov. 22, 1993).

Hanson, L., et al., "Preliminary Evaluation of a New Imaging Bone Densitometer," Presented at the Fourth International Symposium on Osteoporosis, 27–31 Mar., 1993, Hong Kong.

Performance Comparison: Multiple vs. Single Beam X–ray Bone Densitometry, Hologic, Inc. Sep. 1992.

Lunar DP3 User's Manual, Dual–Photon Scanner, pp. 4, 8, 10 and 22 (undated).

Nucletron, A New Dimension In Dual–Photon Absorptiometry, Brochure, Novo Diagnostic (undated).

The Norland Model 2600 Dichromatic Bone Densitometer Brochure, Norland Corp. (undated).

"DPA gaining strength in bone scanning debate", Diagnostic Imaging, Jun. 1986, pp. 102–108.

Osteotek Brochure, models 200 and 300, Medical & Scientific Enterprises, Inc. (undated).

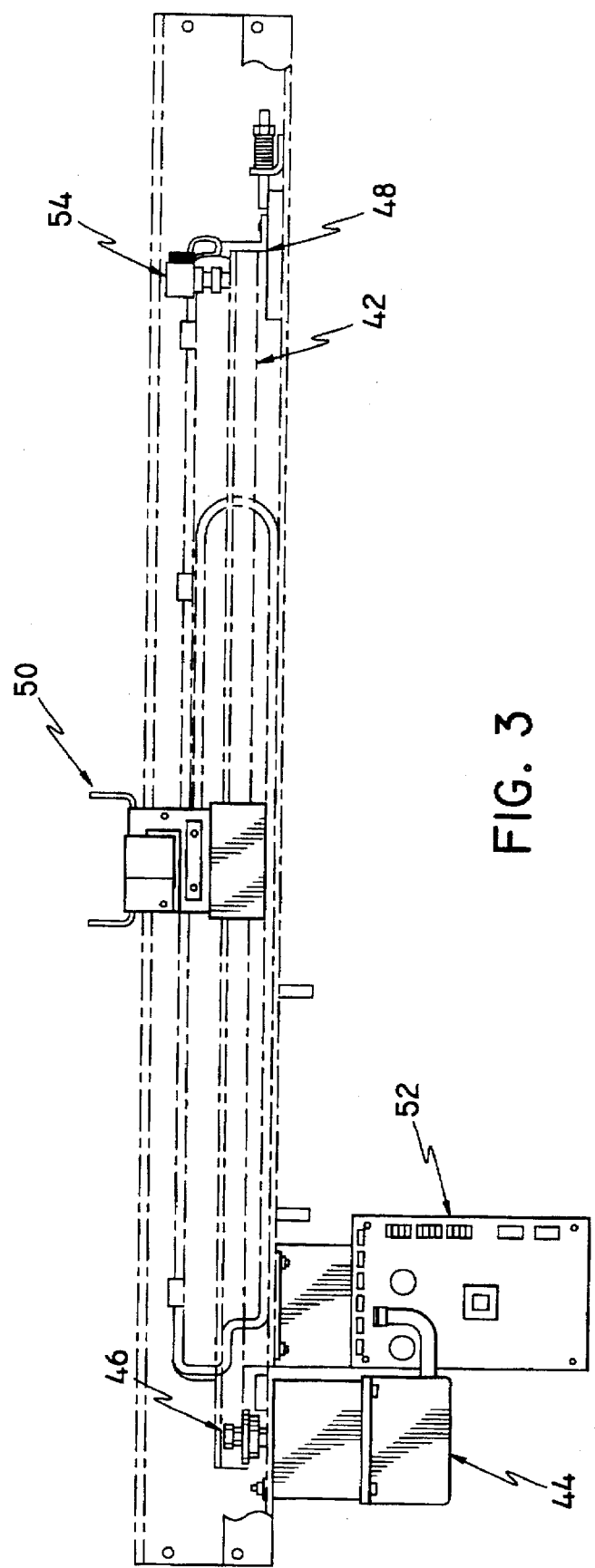

X-RAY BONE DENSITOMETRY USING MULTIPLE PASS SCANNING WITH IMAGE BLENDING

BACKGROUND

1. Field of the Invention

This present invention relates to a method for measuring bone density. More particularly, the present invention relates to a method for measuring bone density with improved image reproduction using overlap blending techniques.

2. Description of the Related Art

X-rays or gamma-rays can be used to measure the density and distribution of bone in the human body in order to help health professionals assess and evaluate projected bone mineral density, which in turn can be used to monitor age-related bone loss that can be associated with diseases such as osteoporosis. Additionally or alternatively, similar procedures can be used to measure non-bone related body content such as body fat and muscle.

In bone densitometry, a patient typically is placed on a table such that the patient's spine extends along the length of the table, along a direction that can be called the Y-axis in Cartesian coordinates. For a supine patient, the left and right sides are in a direction typically called the X-axis. A source at one side of the patient transmits radiation through the patient to a radiation detector at the other side. The source and the detector typically are mechanically linked by a structure such as a C-arm to ensure their alignment along a source-detector axis which is transverse (typically perpendicular) to the Y-axis. Both x-ray tubes and isotopes have been used as a source of the radiation. In each case, the radiation from the source is collimated to a specific beam shape prior to reaching the patient to thereby restrict the field of x-ray or gamma radiation to the predetermined region of the patient opposite which are located the detectors. In the case of using x-rays, various beam shapes have been used in practice including fan beam, pencil beam and cone or pyramid beam shapes. When a fan beam is used, typically the beam conforms to a beam plane which is transverse (e.g., normal) to the Y-axis. Stated differently, the beam is wide in the plane and thin along the Y-axis. The shape of the beam and the shape of the detector system correspond. The detector in a fan beam system typically is an elongated array of detector elements arranged along a line or an arc. By means of mechanically moving the C-arm and/or moving the table, a region of interest in a patient on the table can be scanned with the radiation. Typical regions of analysis in bone densitometry include the spine, hip and forearm scanned individually. They can be covered individually within a reasonable time by a fan beam that has a relatively narrow angle in a single pass or, alternatively, by a pencil beam scanning a raster pattern.

Another analysis region is referred to as "whole body" in which the entire patient body is scanned and analyzed for bone density and possibly also for "body composition" or the percentages of fat and muscle in the body.

X-ray bone densitometry systems have been made by the owner of this application under the tradenames QDR-2000+, QDR-2000, QDR-1500, QDR-1000plus, and QDR-1000. The following commonly owned U.S. patents pertain to such systems and are hereby incorporated by reference herein: U.S. Pat. Nos. 4,811,373, 4,947,414, 4,953,189, 5,040,199, 5,044,002; 5,054,048, 5,067,144, 5,070,519, 5,132,995 and 5,148,455; and 4,986,273 and 5,165,410 (each assigned on its face to Medical & Scientific Enterprises, Inc. but now commonly owned). Other bone densitometry systems are believed to have been made by the Lunar Corporation of Madison, Wis. (see, e.g., the system which is believed to be offered under the tradename Expert and U.S. Pat. Nos. 5,228,068, 5,287,546 and 5,305,368, none of which is admitted to be prior art against this invention).

One system which performs whole body scanning is described in commonly owned application Ser. No. 08/345,069 filed Nov. 25, 1994 which is incorporated herein by reference. The system described therein utilizes a fan beam having a fan angle of about 22 degrees and which is configured to rotate a C-arm for scanning operations.

The system and method according to the present invention provides a cost effective alterative to practitioners from, for example, a higher priced wide fan beam, rotating C-arm scanning system. In addition, the present invention provides whole body scans with a anterior-posterior narrow fan beam projection of the lateral portions of the body (e.g. shoulders, arms and hands). The anterior-posterior narrow beam projection is more directly comparable to scans provided by previous single beam systems than the oblique projections of lateral extremities provided by some rotating C-arm systems.

SUMMARY

Generally, the system of the present invention uses x-rays having a narrow fan beam to scan patients for bone density and soft tissue body composition measurement and imaging. In addition to single pass scanning of body parts, such as the spine, hip and forearm, a method for multiple pass whole body scanning is also provided. A scan pass combination scheme that blends areas of overlap is employed to compensate for errors related to height dependency. The blending is performed according to the height of the part of patient scanned in the overlap and the distance from the edge of the scan pass. Similarly, multiple pass scanning can be applied to large regions of interest other than whole body.

In the preferred embodiment, the system includes a scan table configured to support a patient and define a patient extending in a Y-direction. The scan table is movable in the Y-direction. The Y-direction is defined as parallel to the long axis of the scan table, and the X-direction is transverse to the Y-direction in the plane of the table surface. A C-arm, which is associated with the scan table, is configured to support an x-ray source and an x-ray detector, and is movable in the Y-direction. The source and detector are spatially positioned on opposite sides of the patient.

The x-ray source emits a narrow angle fan beam of x-rays that at any one time irradiates a scan line which extends in the X-direction. The center ray of the x-ray fan beam is parallel to the Z-direction, which is normal to the X-Y plane of the table surface. The detector receives x-rays from the source within the angle subtended by the fan beam after passage through the scan table and patient, producing a substantially anterior-posterior projection of the patient. Preferably, the detector consists of a an array of x-ray detector elements. X-rays which impinge the detector, excite the detector elements which produce analog signals that are converted and collected as digital x-ray attenuation data by a processor. The x-ray source produces pulsed dual energy x-rays that can be filtered sequentially through reference bone and tissue equivalent materials.

The system also provides a drive mechanism which moves the C-arm in the Y-direction and the scan table in both the X-direction and Y-direction. Position encoders, associated with the Y-direction position of the scan table and C-arm, provide position data that can be utilized to process the Y-direction alignment of multiple pass scans. A processor controls the x-ray source, controls movement of the scan table and C-arm, and collects data from the detector array. Also, a processor manipulates the attenuation data to construct scan images and calculate bone density or body tissue composition results.

The present invention also provides a method for whole body scanning. The fan beam and detector array scan the length of the patient in the Y-direction in successive adjacent scan passes. Movement of the C-arm and scan table during each scan pass is preferably continuous. The pattern of scan passes is preferably rectilinear and serpentine to minimize positioning time between passes. Alternative scan patterns, including diagonal patterns are also envisioned.

Scanned data from separate scan passes are combined by a processor to form a contiguous scan. Areas of the patient near the boundary of adjacent passes that are farther in the Z-direction from the focal spot of the x-ray source than the Z-direction distance which the x-ray fan beams intersect, are viewed from two slightly different angles as represented by the two scan passes. It is recognized that perfect registration of overlapping fan beams is possible when objects are at a specific Z-distance from the x-ray source. Moreover, as in stereoscopic vision, acceptable registration of overlapping fan beams can be achieved over some depth of field. Use of the depth of field is optimized in this invention by centering the range around the desired distance individually at each overlapping boundary. Furthermore, this invention extends the effective depth of field by using an algorithm for combining scan passes that blends the area of overlap. Together these aspects of the invention provide a sufficient depth of field in the areas of overlap for the purpose of whole body scanning.

The technique for combining adjacent scan passes, blends each area of overlap at the boundary of the adjacent passes. The number of data points included in each overlap is determined individually as a function of the expected distance in the Z-direction between the x-ray source and the bones or other important features of the patient at the position of the boundary. With blending, the contribution to the combined scan of each data element or data point in the overlap area of each scan pass is proportional to the distance between that data element and the edge of the scan pass.

BRIEF DESCRIPTION OF THE DRAWINGS

A more complete understanding of the invention may be obtained from the following description when taken in conjunction with the drawings, in which:

FIG. 3 is a front view of a diagrammatic representation of a motorized drive system for the examination unit of FIG. 2;

DETAILED DESCRIPTION

Figure 1:
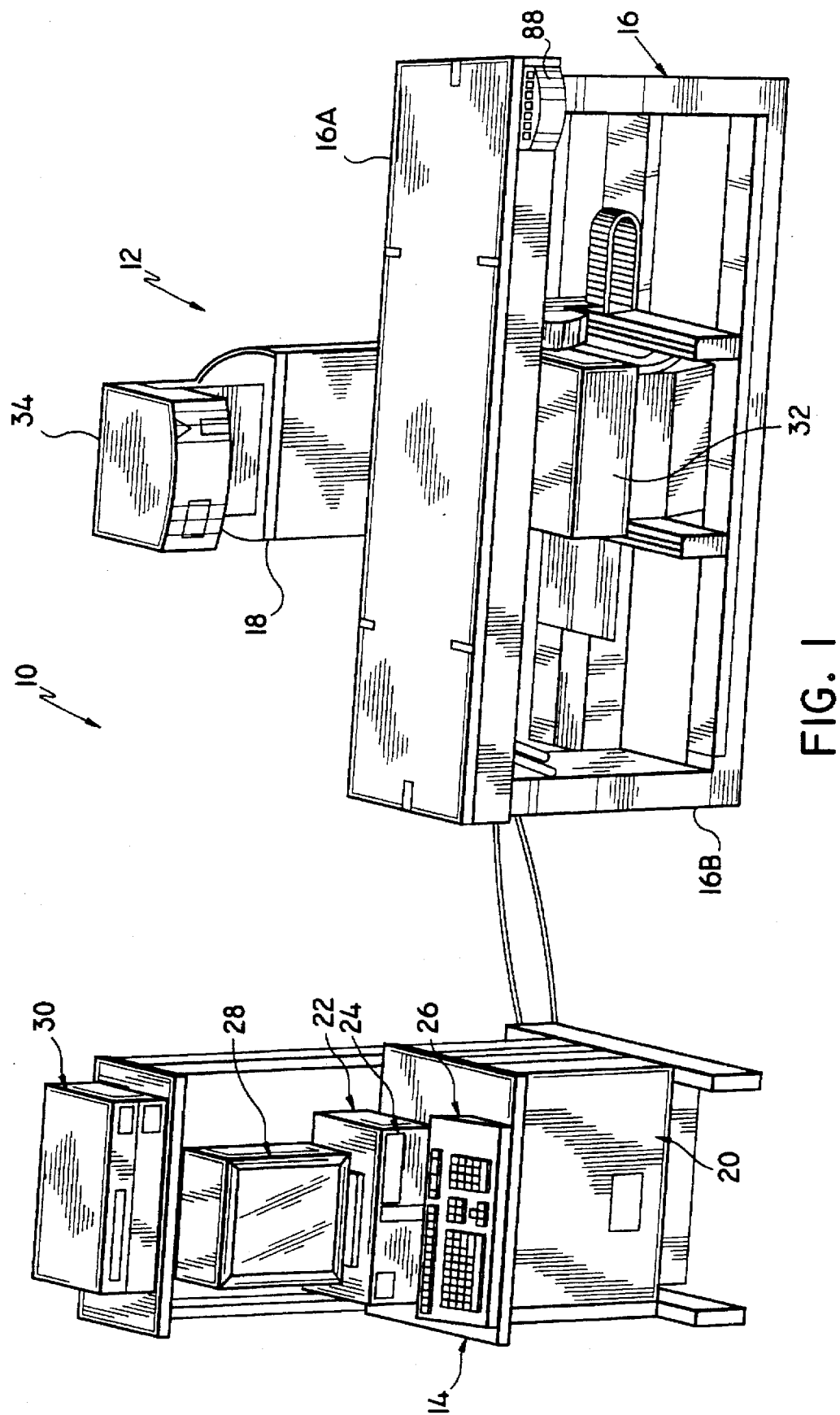
FIG. 1 is a diagrammatic representation of an embodiment of the scanning system according to the present invention, illustrating an examination unit and a workstation.

Referring to FIG. 1, a scanning system 10 includes an examination unit 12 and a work station 14. Workstation 14 includes a system power supply module 20 which provides power to the workstation and/or the examination unit 12, a host computer 22 which has a removable drive recording device 24, e.g., a floppy diskette drive, an operator console keyboard 26, and a display monitor 28. The workstation 14 may also include an optional printer 30. Workstation 14 controls the operation of examination unit 12 and processes scan and position data received from the examination unit into forms more useful for diagnostic purposes, such as into patient images and reports which will be described in more detail below.

The examination unit 12 includes a patient table 16 having a patient support surface 16a and a base 16b, and a C-arm 18 serving as a x-ray source-detector support. Examination unit 12 contains electromechanical components, control systems and other components involved in performing a patient scan and acquiring scan data.

Figure 2:
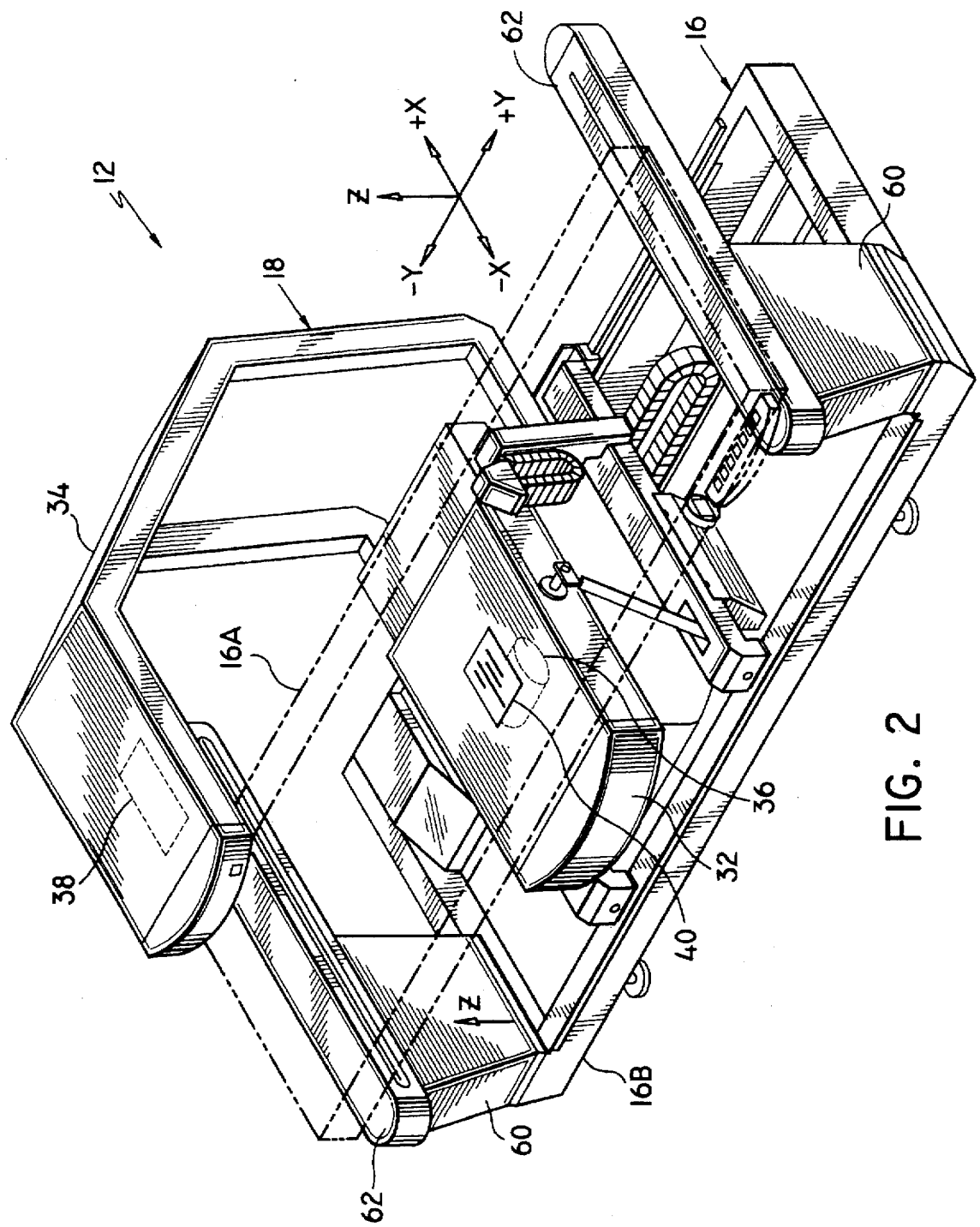
FIG. 2 is a perspective view of the examination unit of FIG. 1.
Figure 2A:
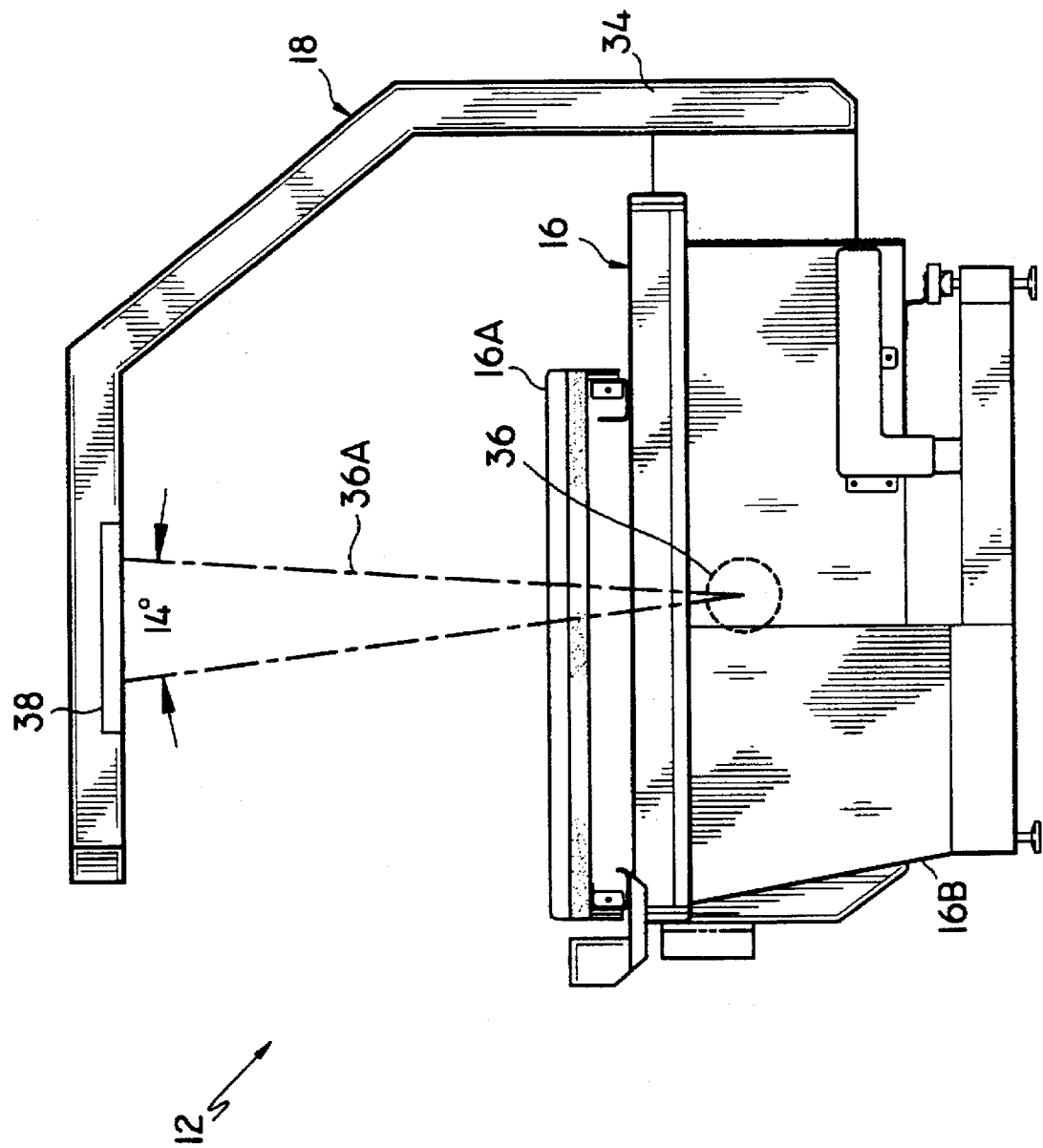
FIG. 2A is a side elevational view of the examination unit of FIG. 1.

An x-ray source 36 is positioned in base 32 and is provided to emit x-rays vertically towards detector 38, as seen in FIG. 2A. In this configuration, x-rays from the x-ray source 36 located beneath patient support surface 16a of table 16 pass through a patient and are received by detector 38. Detector 38 is preferably an array of detector elements, e.g., 64 elements, arranged in a linear configuration extending along the x axis in the XZ plane. Alternatively, the detector elements can be arranged along an arc centered at the focal spot in the x-ray tube. Detector 38 is about 10 inches long in the X direction and is about 42 inches from the origin of beam 36a (i.e., a 0.16 inch detector-to-detector spacing) and subtends a fan angle of about 14 degrees. Preferably, the detector elements that make up the array are silicon photo diodes coupled with a scintillation material, and they are fixed with respect to x-ray source 36. Other types of detector elements are also contemplated. Each detector element responds to x-rays at respective angular positions within a fan beam of x-rays and provide scan data to computer 22 in workstation 14. In this exemplary embodiment, x-ray source 36 has a stationary anode, and is a dual-energy (DE) pulse system that is synchronized to the alternating current system power source.

Continuing to refer to FIGS. 2 and 2A, a slit collimator 40 is positioned between source 36 and the patient. Collimator 40 has one or more selectable slits machined or otherwise formed to allow the passage of x-rays through a slit from source 36 to the patient, and is made of an x-ray opaque material, such as lead or tungsten, of sufficient thickness to substantially block the passage of x-rays through portions of the collimator other than through the slits. For example, collimator 40 has a 64 mm long collimator slit positioned an appropriate distance from the focal spot in source 36 and suitably aligned therewith. The x-ray radiation from x-ray source 36 passes through the selected slit in the collimator 40 and forms a fan shaped beam of x-rays 36a. The angle subtended by beam 36a and the distance between its origin at the focal spot of the x-ray tube and the patient are selected such that beam 36a would not cover the entire cross-section of a typical adult patient at any one time but would cover only a selected portion of that width.

Fan beam 36a has a narrow fan angle which ranges from between about 0.2 degrees and about 30 degrees. Preferably, the fan angle is 14 degrees. Of course, x-ray beam 36a not only has width (along the X-axis illustrated in the figures) but also has a thickness along the Y-axis that is defined by the width of the slit in collimator 40 (which can be, e.g., 1.0 mm) and distance from the origin of beam 36a. A scan line is defined by the portion of the patient imaged at any one time with fan beam 36a and with detector 38, i.e., the width and thickness of the x-ray beam over which data is collected at one point in time. While the term scan line is used, it should be clear than this "line" in fact is a rectangle that has both a width in the x-direction and length in the y-direction. A complete scan consists of one or a set of adjacent scan passes obtained over a period of time such that the entire region of interest has been measured. The scanning apparatus may also include an x-ray beam modulator (not shown) which is typically positioned between the collimator 40 and the patient. Beam modulators modulate x-ray beam 36a in a periodic pattern for certain types of diagnostic scanning. An adjustable x-ray beam attenuator (not shown) may also be provided for changing the intensity and/or energy spectrum of x-ray beam 36a as desired for different scans and/or other purposes.

System Scanning Motions

Figure 4:
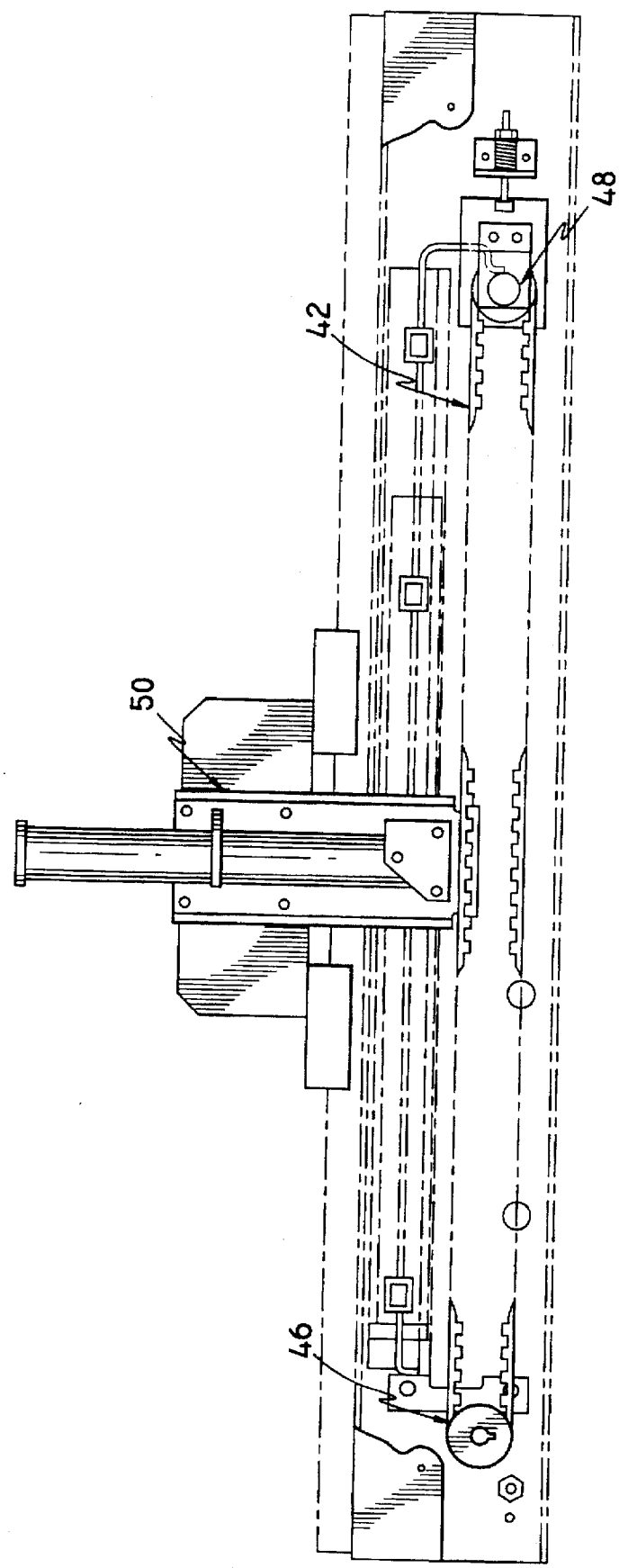
FIG. 4 is a top view of the diagrammatic representation of FIG. 3.

Referring now to FIGS. 2-4, the patient table 16 is translatable along two axes—the longitudinal (Y axis) and the transverse (X axis). As seen in FIGS. 3 and 4, table 16 can be driven in the positive and in the negative directions along the Y-axis by using a toothed drive belt 42 driven by a stepper motor 44 through a drive pulley 46 and an idler pulley 48. Belt 42 is secured to a table bracket 50, which in turn is secured to patient support surface 16a of table 16. A motor controller board 52 controls motor 44. Generally, controller board 52 is coupled to computer 22 in workstation 14 and activates the motor in response to commands or instructions from computer 22. A DC servo motor can be used in place of stepper motor 44, and other drive implementations can be substituted, such as stepper-motor driven lead-screws. Each motion of the patient support surface 16a is computer controlled and monitored by an absolute encoder feedback system receiving feedback information from an absolute encoder 54. Encoder 54 is coupled with idler pulley 48 to provide information to the computer 22 respecting any rotation of that pulley and thereby respecting any motion of belt 42 and patient support surface 16a of table 16 in each direction along the Y-axis. One or more encoders may be used to track the position of patient support surface 16a. The position data from the encoder or encoders is transferred to computer 22 for processing.

In addition, as noted above, patient support surface 16a of table 16 selectively moves left and right along the X-axis. Table 16 is driven in each direction along the X-axis under computer control by motors and lead screw or belt mechanisms in the upper portions 62 of pedestals 60, using motor control and absolute encoder feedback as described earlier for the table motion along the Y-axis.

Figure 2B:
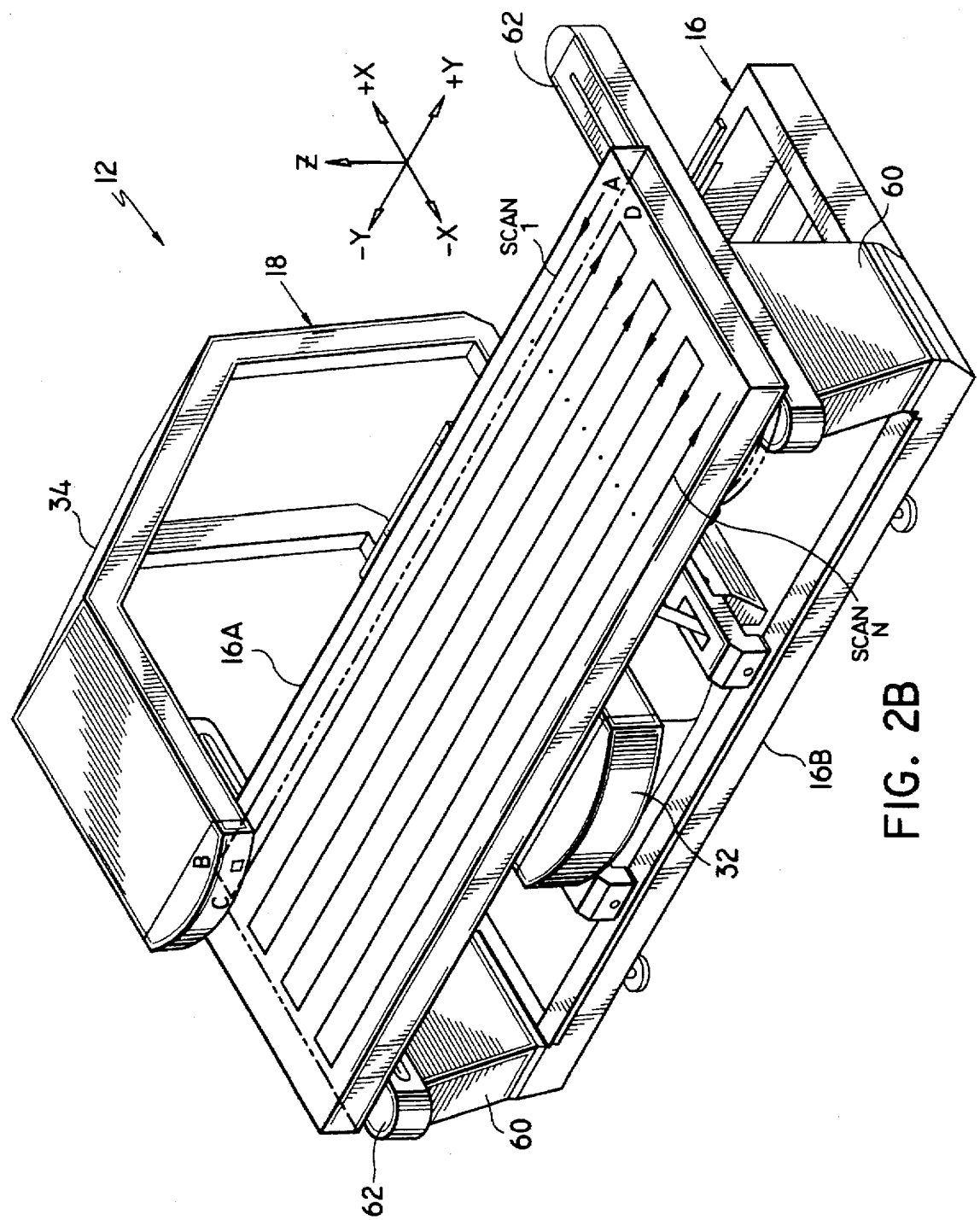
FIG. 2B is a perspective view of the examination unit similar to FIG. 2 and illustrating an exemplary scanning motion of the scanning apparatus.

Referring to FIG. 2B, to perform a whole body scan, a series of scans or scan passes (identified as scans 1 to N, in FIG. 2B) of data are acquired. The data received from the scans is referred to as scan data which is subsequently processed by computer 22 to determine bone density and to provide, e.g., an image on monitor 28.

In the preferred embodiment, the table 16a moves in a continuous motion along the Y-axis, and simultaneously the C-arm 18 moves in a continuous motion in the opposite direction along the Y-axis. Consequently, the position of the fan beam is moved from an initial position "A" to an end position "B" on the table surface. Once at the end position, the table 16a is moved along the X-axis a predefined distance of about 3.6 inches to a new initial position "C" for the next scan pass. The table and C-arm then move back in the Y-axis to position the fan beam at end position "D". This procedure is continued until the patient position associated with the patient support surface 16a is completely scanned. Each of the C-arm 18 and table 16a moves a distance in the Y-axis which is about half the total length of the patient. Thus, the fan beam moves in a rectilinear serpentine pattern relative to the patient support surface to expose the entire body of the patient to the scanning x-rays. A typical whole body scan consists of seven scan passes. Alternative embodiments may exclude movement of the table 16a. However, such embodiments would require a longer throw for the Y-axis movement of the C-arm and hence a longer base 16b for the system. Also, other possible scan patterns are contemplated. For example, the scan pattern may be diagonal.

Scanner Electrical and Electronic Control Systems

Figure 5:
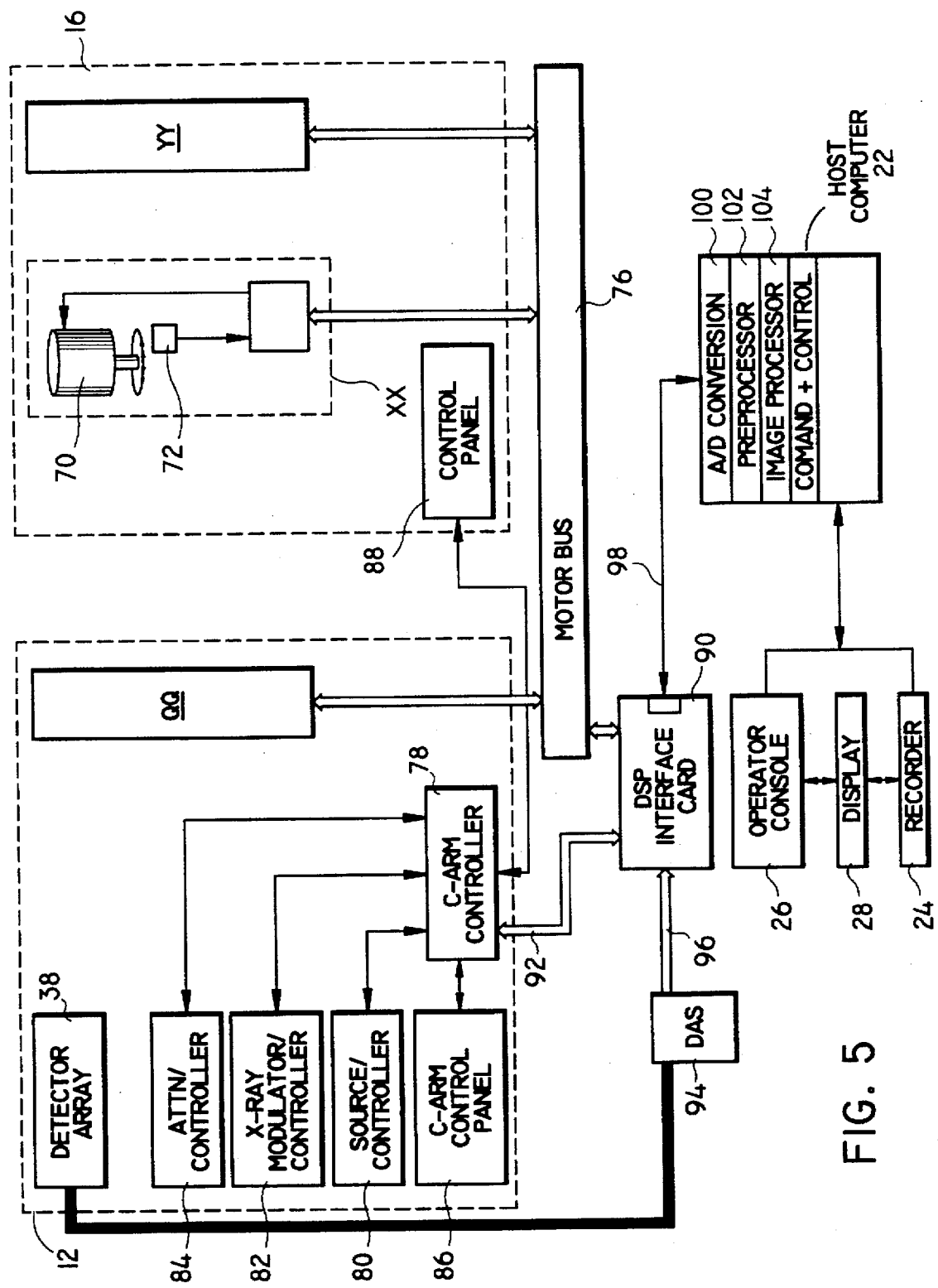
FIG. 5 is a block diagram of the electric and electronic systems of the scanning system of FIG. 1.

Referring to FIG. 5, the electrical and electronic control systems of an embodiment in accordance with the invention will be described. Examination unit 12 includes the structure illustrated in FIGS. 1 and 2, as well as a suitable power supply module 20 for x-ray source 36 and motors for driving patient table 16 and C-arm 18, and to operate an attenuator and modulator (not shown). Each of the motors has a local controller with motor driver electronics and position encoder. A detailed description of the encoder and their operation is provided in application Ser. No. 08/345,069 filed Nov. 25, 1994 which is incorporated herein by reference. As seen in FIG. 5, the drive system XX which causes X direction translation of patient support surface 16a of table 16 is shown as including a motor 70, a motor position encoder 72 and local X motion controller/motor driver electronics 74. For the sake of brevity, similar structure for the Y direction translation of the patient table is shown as block YY. Block QQ denotes the C-arm translation in the Y direction. The local controllers for drive systems XX, YY and QQ communicate over motor bus 76.

As further shown in FIG. 5, the C-arm 18 has a C-arm local controller 78, which communicates with x-ray source controller 80, x-ray modulator controller (which includes CPU 82), x-ray attenuator controller 84 and control panels 86 and 88 which are located in the C-arm 18 and patient table 16, respectively. C-arm controller 78 communicates via C-arm controller bus 92.

Detector array 38 supplies x-ray measurements (scan data) to data acquisition system (DAS) 94, where the measurements are collected and can be preliminarily processed. The DAS 94 outputs its collected and processed x-ray measurements from the individual elements of detector array 38 via DAS bus 96.

Digital Signal Processor (DSP) 90 is coupled to each of the motor bus 76, C-arm controller bus 92, and DAS bus 96, and functions as a communications exchange for the remote controllers with host computer system 22. While use of a digital signal processor 90 is shown in this embodiment, it is contemplated that any known system which can network communications between the various local processors and the host computer 22 can be used in connection with this invention. DSP 90 includes an interface for communication with the host computer in conventional fashion, such as by an ISA bus or through an industry standard interface on the card (e.g., SCSI, IEEE 488, etc.) to a communications line 98.

Use of distributed processing and communications networking between a plurality of local processor controllers via the DSP 90 interface, reduces wiring complexity between various controlled devices and the host computer system 22. DSP 90 is responsible for real-time processing, such as motion control over table 16 and C-arm 18. Host computer 22 also has the advantage of having a more integrated and consistent datastream content in the DSP 90 data buffers than would be communicated by all of the separate local controllers. For example, both scan data from the DAS 90 and its corresponding position data obtained from the patient table 16 and C-arm 18 position encoders (e.g., 72) can be contained in the same data buffers.

Host computer 22 provides central command and control of the entire scanner system. In the embodiment shown herein, host computer 22 is an IBM AT-compatible architecture computer, having therein an 80486/25 MHz or higher clock rate microcomputer, manufactured by Intel or equivalent vendor product.

In order to perform scan data processing, the ultimate goal of the scanning system, scan data from the DAS 94 is forwarded to the host computer 38, which is programmed to perform A/D conversion at 100 and preliminary data preprocessing at 102 similarly to the QDR-2000 and QDR-2000+ systems mentioned in the background. The output of the preliminary data preprocessing functions 102 is supplied to another image processing program 104, which performs various calculations and forms an image in a manner similar to that used in the earlier systems noted above, and additionally, blends the data from successive scans, as will be described below. While the A/D conversion 100, preprocessing 102 and image processing 104 functions can be performed by the host computer 22, executing program modules, those functions can be performed in separate, dedicated data processing apparatus.

Data and images from processor program 104 are supplied to a console 26, display 28 and a recorder (e.g., floppy disk drive 24 and/or a printer 30) for purposes and in a manner similar to those in the earlier systems. Two-way arrows connect the elements of FIG. 5 to illustrate the fact that two-way communications can take place therebetween. Conventional elements have been omitted from the Figures and from this description for the sake of conciseness.

Image Blending

Figure 6:
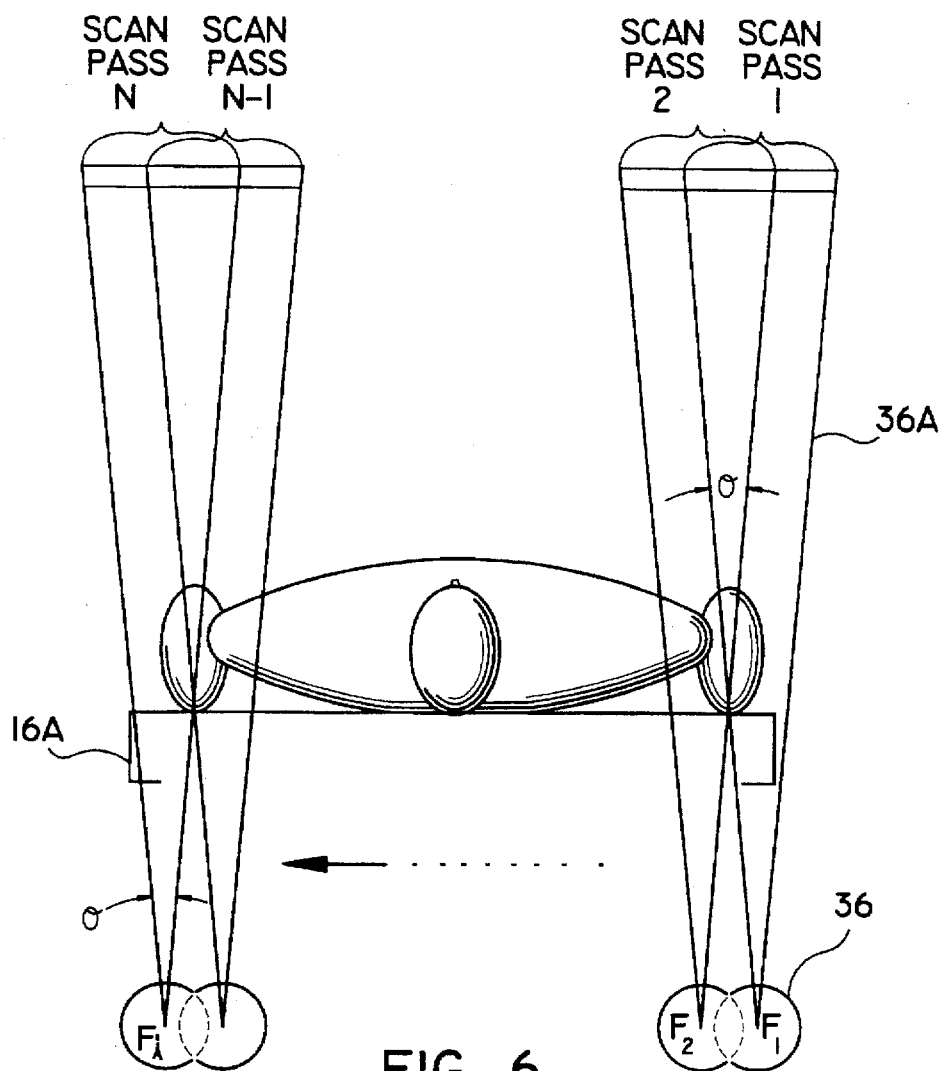
FIG. 6 is a representation of x-ray fan beam coverage of a patient for whole body measurement, illustrating multiple scan passes.
Figure 6A:
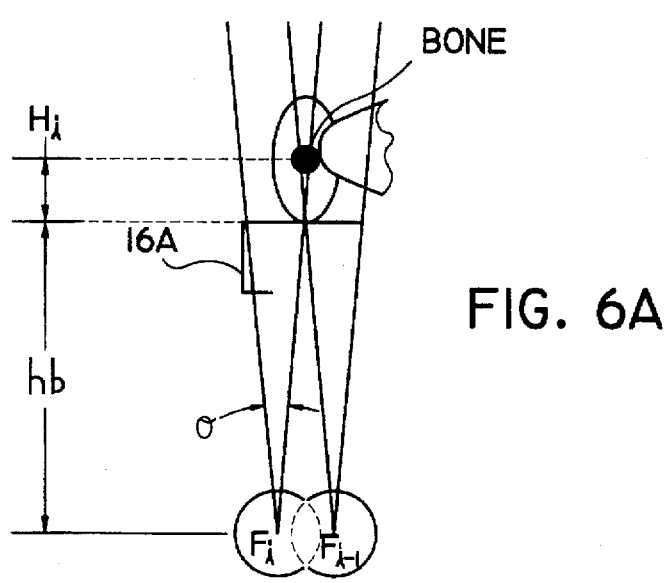
FIG. 6A is a representation of a portion of the x-ray fan beam coverage of FIG. 6 greatly enlarged, illustrating an estimated patient height from the focal point of the x-ray source.

Multiple pass scans provided by the system described above have an area of overlap between adjacent scan passes. This beam overlap is illustrated in FIG. 6 and the angle "Θ" represents the angel of overlap between scans, e.g., scan 1 and scan 2. The angle of overlap is limited by the constraints of the system (e.g. fixed C-arm 18 angle and fixed scan table 16a height) to be equal to the angle of the fan beam.

To compensate for the beam overlap produced height dependencies, the present invention utilizes an image or scan blending technique in the combination of scan passes. The technique combines the scan data by an amount which is a function of the height of the middle of the patient (or important bone features of the patient) at the expected position of the overlap and the distance from the edge of the scan pass. The height assumptions are stored or entered in the computer 22. The preferred heights, for example, for an adult for the six overlaps of a seven pass scan are 1.5, 2.5, 2.0, 2.0, 2.5 and 1.5 inches respectively. Scan selections with customized heights for various patient characteristics (e.g. large, medium, small, male, female, adult, child, etc.) are also contemplated.

Figure 7:
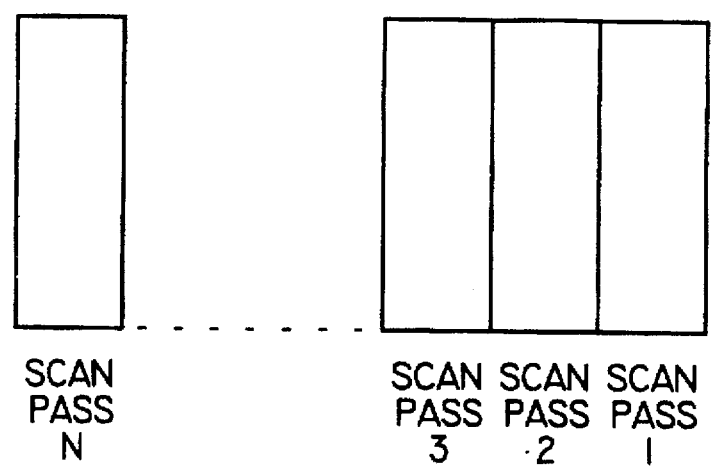
FIG. 7 is a representation of a memory map storing each scan pass prior to blending.
Figure 8:
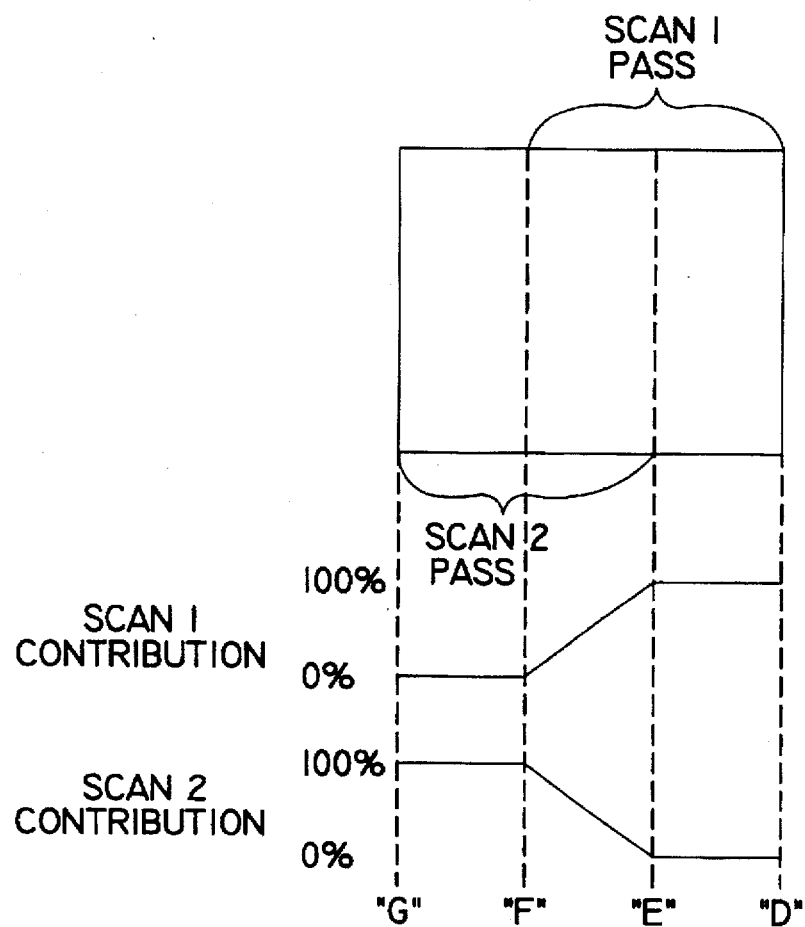
FIG. 8 is a representation of a memory map storing each scan pass after blending and a corresponding blending contribution graph for each scan pass.

To illustrate, FIG. 7 provides an exemplary memory map for storing scan data in memory for each scan pass. The data for each scan pass is stored in adjacent scan blocks (identified as scan blocks 1-N). FIG. 8 illustrates a memory map after combining the overlap portions of each scan pass and the weighted contribution of each scan pass in the resulting scan array. From the edge "D" of scan 1 to the edge of "E" where the overlap begins, the weighted contribution by scan 1 is about 100% and the contribution of scan 2 is about 0%. When in the overlap region, defined by the increases or decreases, the contribution of scan pass 1 decreases from about 100% to about 0%, while the contribution of scan pass 2 increases from about 0% to about 100%. From the edge "F" where the overlap region ends to the edge of "G" of scan pass 2, the weighted contribution by scan 1 is about 0% and the contribution of scan pass 2 is about 100%.

Adjacent scan passes are positioned in the X-axis such that the outer rays of the fan beam from each pass intersect preferably at or before the patient surface. The distance from the focal spot, in the Z-direction, at which the fan beams intersect is given by the following equation:

$$D_i = \frac{|F_{i+1} - F_i|}{2\tan\frac{\Theta}{2}} \qquad \text{Eq. 1}$$

where $F_i$ is the position of the focal spot of the x-ray source for each pass i, and $\Theta/2$ is the half of the angle subtended by the fan beam.

An exemplary algorithm for combining data elements (data points) in adjacent scan passes acquired by the scanning system of the present invention is represented by equations 2 and 3 below. Equation 3 provides a blending of overlap data that is a linear function of the distance from each data element to the edge of the scan pass. Other mathematical functions (e.g., quadratic and exponential) that could be employed as a function of distance from the scan pass edge are also contemplated. The algorithm of equations 2 and 3 is general in that the height at which the rays of adjacent fan beams intersect can be set arbitrarily by choosing the distance between focal spots.

The array ST represents a scan line of the resulting scan. Arrays $S_i$ are the corresponding data lines from each pass i. As such, ST[x] and $S_i$[x] are data elements in the arrays ST and $S_i$, respectively. Equations 2 and 3 are repeated for each pass i from 1 to N to construct a complete scan line.

For each point x, where $v_{i-1} \leq x_i < nd - v_i$, there is no overlap and the resulting array ST is given by:

$$ST[xt_{i-1}+x] = S_i[x] \qquad \text{Eq. 2}$$

For each point x, where $nd - v_i \leq x_i \leq nd$, there is overlap and the resulting array ST is given by:

$$ST[xt_{i-1}+x] = \left(\frac{1}{v_i}\right)((nd-x)S_i[x] + \qquad \text{Eq. 3}$$
$$(v_i - (nd-x))S_{i+1}[v_i - (nd-x)])$$

where $xt_i$ is the total number of points in the constructed scan line after pass i and is given by equation 4:

$$xt_i = xt_{i-1} + nd - v_i \qquad \text{Eq. 4}$$

and $v_i$ is the number of overlap data points in scan pass i and is defined by equations 5a, 5b and 5c:

when $i = 0$, then $$v_0 = 0 \qquad \text{Eq. 5a}$$

when $0 < i < N$, then $$v_i = \frac{2(H_i + hb)\left(\tan\frac{\theta}{2}\right) - |F_{i+1} - F_i|}{xd} \qquad \text{Eq. 5b}$$

when $i = N$, then $$V_N = 0 \qquad \text{Eq. 5c}$$

and where:

nd is the number of data points in every line of each scan pass;

$H_i$ is the height of the patient above the scan table in the overlap of scan pass i and scan pass i+1;

hb is the height of the scan table above the focal spot;

$\Theta/2$ is the half angle of the x-ray fan beam;

$F_i$ is the location of the focal spot in scan pass i; and xd is the x-dimension size of each data point of each scan pass.

As described above, in the general algorithm the distance from the focal spot at which the fan beams intersect may be arbitrarily set. In instances where the distance between the x-ray source focal spots in adjacent scan passes is such that the fan beams of the adjacent passes intersect approximately at the top of the surface of the scan table, then the following simplification of equation 5 above occurs.

$$2hb\left(\tan\frac{\theta}{2}\right) = |F_{i+1} - F_i| \qquad \text{Eq. 6}$$

As a result, the number of overlap data points $v_i$ in each scan pass i reduces to:

$$v_i = \frac{2H_i \tan\frac{\theta}{2}}{xd} \qquad \text{Eq. 7}$$

As such, equations 2 and 3 above represent the resulting scan array ST, except that the overlap data points $v_i$ is substituted in equations 2 and 3.

It will be understood that various modifications can be made to the embodiments of the present invention herein disclosed without departing from the spirit and scope thereof. For example, various drive mechanisms may be employed to move the support surface or the C-arm, as well as various processors may be utilized to perform the blending operation. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. An x-ray bone densitometry system, which comprises:

a table having a patient support surface configured to support a patient and define a patient position extending in a Y-direction, said surface being movable in said Y-direction and in an X-direction;

a C-arm associated with said table and movable in said Y-direction, said C-arm being configured to support an x-ray source in opposition to an x-ray detector at opposite sides of the patient, said x-ray source emitting a narrow angle fan beam of x-rays which at any one time irradiates a scan line which extends in said X-direction, and said x-ray detector receiving x-rays from said source within the angle of said fan beam after passage thereof through at least a portion of said patient position to generate scan data therefrom;

a scanning mechanism configured to move said patient support surface and said C-arm to scan the patient position with said narrow angle fan beam in successive scan passes along directions that are transverse to the X-direction but are selectively displaced in said X-direction relative a preceding scan pass; and a processor configured to actuate said scanning mechanism, to receive said scan data and to combine said scan data from each of said scan passes to form composite scan data, said processor being configured to combine said scan data such that data elements in said scan pass that overlap an adjacent scan pass are weighted proportionally as a function of a distance from an edge of said scan pass and a predetermined height of a portion of the patient at the overlap.

2. The system according to claim 1, wherein said processor defines the amount of said overlap as a function of a selectable distance of patient from a focal spot of said x-ray source.

3. The system according to claim 2, wherein said selectable distance is individually selectable for each of said scan passes.

4. An x-ray bone densitometry system, which comprises:

a table having a patient support surface configured to support a patient and define a patient position;

a C-arm associated with said table and movable relative to said patient support surface in the X-Y plane, said C-arm being configured to support an x-ray source and an x-ray detector opposite a patient in said patient position, said x-ray source emitting a narrow angle fan beam of x-rays which irradiates a portion of said patient position, and said x-ray detector having an array of detecting elements configured to receive x-rays from said source within an angle subtended by said fan beam after passage thereof through the patient position and to generate scan data therefrom;

a drive system configured to move said C-arm relative to said patient support surface in said X-Y plane and to scan the patient position with said fan beam in successive scan passes, wherein said beams in successive scan passes partially overlap each other at the height of the patient position; and a processor configured to receive said scan data and to combine said scan data to form composite scan data, said processor being configured to combine said scan data such that data elements in said pass that overlap an adjacent scan pass are weighted proportionally as a function of a distance from an edge of said scan pass and a predetermined height of a portion of the patient at the overlap.

5. The system according to claim 4, wherein the amount of said overlap is defined as a function of a user selectable distance of the patient from a focal spot of said x-ray source.

6. The system according to claim 5, wherein said selectable distance is individually selectable for each of said scan passes.

7. A method for multiple pass whole body scanning using a fan beam bone densitometer, comprising:

positioning a patient on a patient support surface of a scan table;

irradiating the patient with a fan beam of x-rays subtending an angle that includes substantially less than the body width of the patient;

receiving x-rays from the source within the angle subtended by the fan beam after passage thereof through the patient at a number of radiation detecting positions arrayed within said angle;

scanning the fan beam and detector along the patient in successive passes and selectively moving at least one of said patient support surface and said fan beam along each of two orthogonal axis in the plane of the patient position to scan the entire patient with a rectilinear serpentine pattern of partially overlapping scan passes; and combining said successive scan passes such that data elements in each scan pass that are determined to overlap an adjacent scan pass contribute to the combined scan with a weighing that is a function of the distance between said data element and an edge of said scan pass that overlaps said adjacent scan pass, said weighing being proportional to said distance and a predetermined height of a portion of the patient at the overlap.

8. The method according to claim 7, wherein the amount of said overlap is determined as a function of a selective distance, normal to the plane of the patient, from the focal spot of said x-ray source to the bones of the patient in the overlap area.

9. A method for multiple pass scanning using a fan beam bone densitometer, comprising:

positioning a patient on a patient support surface of a scan table;

irradiating the patient with a fan beam of x-rays subtending an angle that includes substantially less than the body width of the patient;

receiving x-rays from the source within the angle subtended by the fan beam after passage thereof through the patient at a number of radiation detecting positions arrayed within said angle;

scanning the fan beam and detector along the patient in successive passes and selectively moving at least one of said patient support surface and said fan beam along each of two orthogonal axis in the plane of the patient position to scan at least a region of the patient with at least two partially overlapping scan passes; and combining said successive scan passes such that data elements in each scan pass that are determined to overlap an adjacent scan pass contribute to the combined scan with a weighing that is a function of the distance between said data element and an edge of said scan pass that overlaps said adjacent scan pass, said weighing being proportional to said distance and a predetermined height of a portion of the patient at the overlap.

10. The method according to claim 9, wherein the amount of said overlap is determined as a function of a selective distance, normal to the plane of the patient, from the focal spot of said x-ray source to the bones of the patient in the overlap area.

* * * * *